United States Patent
Rucker et al.

(10) Patent No.: US 12,251,318 B2
(45) Date of Patent: Mar. 18, 2025

(54) SURGICAL IMPLANT DEVICE INCORPORATING A LATTICE VOLUME AND ASSOCIATED METHOD OF MANUFACTURE

(71) Applicant: Kyocera Medical Technologies, Inc., Redlands, CA (US)

(72) Inventors: Scott Alan Rucker, Austin, TX (US); Joseph Virgil Thompson, Round Rock, TX (US); Gregory N. Glazner, Austin, TX (US); Trace Cawley, Austin, TX (US)

(73) Assignee: Kyocera Medical Technologies, Inc., Redlands, CA (US)

( * ) Notice: Subject to any disclaimer, the term of this patent is extended or adjusted under 35 U.S.C. 154(b) by 0 days.

(21) Appl. No.: 17/072,111

(22) Filed: Oct. 16, 2020

(65) Prior Publication Data
US 2022/0117753 A1   Apr. 21, 2022

(51) Int. Cl.
*A61F 2/44* (2006.01)
*A61F 2/30* (2006.01)

(52) U.S. Cl.
CPC .......... *A61F 2/4455* (2013.01); *A61F 2/3094* (2013.01); *A61F 2/442* (2013.01);
(Continued)

(58) Field of Classification Search
CPC .............. A61F 2/442; A61F 2002/4435; A61F 2002/4445; A61F 2002/30011;
(Continued)

(56) References Cited

U.S. PATENT DOCUMENTS

| 9,549,823 | B2 | 1/2017 | Hunt et al. |
| 10,154,913 | B2 | 12/2018 | Steinmann et al. |

(Continued)

FOREIGN PATENT DOCUMENTS

| CN | 103561689 B | 1/2016 |
| CN | 208274654 U | 12/2018 |

(Continued)

OTHER PUBLICATIONS

International Search Report issued in Corresponding PCT Application No. PCT/US2021/055134.
(Continued)

*Primary Examiner* — Christopher D. Prone
(74) *Attorney, Agent, or Firm* — Clements Bernard Walker; Christopher L. Bernard; Devin Cummins

(57) ABSTRACT

The present disclosure provides a surgical implant device, including: a solid surface; and a lattice structure disposed adjacent to the solid surface, wherein the lattice structure includes a first plurality of struts that define a first plurality of voids adjacent to the solid surface and a second plurality of struts that define a second plurality of voids remote from the solid surface. Each of the first plurality of struts has an average cross-sectional diameter that is smaller than an average cross-sectional diameter of each of the second plurality of struts. Each of the first plurality of voids has an average internal diameter that is smaller than an average internal diameter of each of the second plurality of voids. The surgical implant device also includes a needle-populated porous surface disposed adjacent to the solid surface opposite the lattice structure.

10 Claims, 11 Drawing Sheets

(52) U.S. Cl.
CPC ............... *A61F 2002/30011* (2013.01); *A61F 2002/30985* (2013.01); *A61F 2002/4435* (2013.01); *A61F 2310/00011* (2013.01)

(58) Field of Classification Search
CPC ........ A61F 2/4455; A61F 2/44; A61F 2/3094; A61F 2310/00011
See application file for complete search history.

(56) References Cited

U.S. PATENT DOCUMENTS

| | | | |
|---|---|---|---|
| 10,369,009 | B2 | 8/2019 | Joly et al. |
| 10,413,427 | B2 | 9/2019 | Trieu |
| 10,524,927 | B2 | 1/2020 | Ryan |
| 10,561,456 | B2 | 2/2020 | Cawley et al. |
| 2014/0107786 | A1 | 4/2014 | Geisler et al. |
| 2015/0018956 | A1 | 1/2015 | Steinmann et al. |
| 2018/0110624 | A1 | 4/2018 | Arnone |
| 2018/0243097 | A1 | 8/2018 | Jones et al. |
| 2018/0256336 | A1 | 9/2018 | Mueller et al. |
| 2019/0083270 | A1 | 3/2019 | Milz et al. |
| 2019/0133783 | A1* | 5/2019 | Unger ...................... A61F 2/44 |
| 2019/0151113 | A1 | 5/2019 | Sack |
| 2019/0183653 | A1 | 6/2019 | Gregersen et al. |
| 2019/0254840 | A1 | 8/2019 | Gray et al. |
| 2019/0298525 | A1 | 10/2019 | Wright et al. |
| 2020/0000595 | A1 | 1/2020 | Jones et al. |
| 2020/0179123 | A1 | 6/2020 | Steinmann et al. |
| 2020/0261243 | A1 | 8/2020 | Unger et al. |
| 2020/0323646 | A1 | 10/2020 | Picha et al. |

FOREIGN PATENT DOCUMENTS

| | | |
|---|---|---|
| CN | 208287107 U | 12/2018 |
| CN | 106510906 B | 1/2019 |
| CN | 107252373 B | 2/2019 |
| CN | 208598587 U | 3/2019 |
| CN | 208611050 U | 3/2019 |
| CN | 109730814 A | 5/2019 |
| CN | 109966027 A | 7/2019 |
| CN | 111529144 A | 8/2020 |
| JP | 2018537235 A | 12/2018 |
| WO | 2016130878 A | 8/2016 |

OTHER PUBLICATIONS

Oct. 8, 2024 European Search Reported issued in corresponding EP Application No. 21881154.
Final Action Decision of Refusal dated Nov. 19, 2024 issued in corresponding JP App.: 2023-548532.

* cited by examiner

SURGICAL IMPLANT DEVICE INCORPORATING A LATTICE VOLUME AND ASSOCIATED METHOD OF MANUFACTURE

TECHNICAL FIELD

The present disclosure relates generally to the surgical and medical device fields. More particularly, the present disclosure relates to a surgical implant device incorporating a lattice volume and an associated method of manufacture.

BACKGROUND

A variety of conventional surgical implant devices, such as spinal and other orthopedic implant devices, exist that incorporate internal voids that are intended to impart such surgical implant devices with a degree of elasticity and provide areas for bone graft placement and bony ingrowth and purchase, while attempting to maintain structural integrity and strength, especially when such surgical implant devices are manufactured from metallic and/or polymeric materials. Weight savings may also be a consideration in some applications. These internal voids may take the form of discrete holes and/or pores, strut assemblies, and/or lattice volumes, for example. However, to date, such conventional surgical implant devices do not perform adequately and/or are difficult to manufacture.

SUMMARY

In various illustrative embodiments, the present disclosure provides a surgical implant device, such as a spinal or other orthopedic implant device, that that incorporates both solid surfaces and an internal lattice volume. Specifically, an anterior lumbar interbody fusion (ALIF) cage is provided as an example. This internal lattice volume utilizes more numerous, smaller pores and fine struts adjacent to the solid surfaces and less numerous, larger pores and thicker struts remote from the solid surfaces, thereby providing superior elasticity, bony ingrowth and purchase, and structural integrity and strength properties. Conventional internal voids and the like may also be provided for bone graft placement, etc. The surgical implant device of the present disclosure is developed using a computer-aided design (CAD) model and manufactured from a metallic (e.g., titanium) or polymeric (e.g., polyether ether ketone (PEEK)) material using an additive manufacturing process, such as three-dimensional (3D) printing, or a more traditional manufacturing process.

In one illustrative embodiment, the present disclosure provides a surgical implant device, including: a solid surface; and a lattice structure disposed adjacent to the solid surface, wherein the lattice structure includes a first plurality of struts that define a first plurality of voids adjacent to the solid surface and a second plurality of struts that define a second plurality of voids remote from the solid surface. Each of the first plurality of struts has an average cross-sectional diameter that is smaller than an average cross-sectional diameter of each of the second plurality of struts. Each of the first plurality of voids has an average internal diameter that is smaller than an average internal diameter of each of the second plurality of voids. The first plurality of struts and the first plurality of voids have an overall material density that is approximately equal to the second plurality of struts and the second plurality of voids. Optionally, the lattice structure further includes a third plurality of struts that define a third plurality of voids disposed between and coupling the first plurality of struts and the first plurality of voids and/to the second plurality of struts and the second plurality of voids. Optionally, the solid surface is disposed at an external periphery of the surgical implant device. Alternatively, the solid surface is disposed at an internal portion of the surgical implant device. The solid surface and the lattice structure are integrally formed. The surgical implant device also includes a needle-populated porous surface disposed adjacent to the solid surface opposite the lattice structure. The solid surface and the needle-populated porous surface are integrally formed.

In another illustrative embodiment, the present disclosure provides a method for manufacturing a surgical implant device, including: designating a portion of a virtual volume as a solid surface; selecting a first plurality of points within the virtual volume adjacent to the solid surface that locate a first plurality of struts that define a first plurality of voids; selecting a second plurality of points within the virtual volume remote from the solid surface that locate a second plurality of struts that define a second plurality of voids; locating the first plurality of struts that define the first plurality of voids within the virtual volume using the first plurality of points; and locating the second plurality of struts that define the second plurality of voids within the virtual volume using the second plurality of points. The method also includes thickening each of the first plurality of struts and the second plurality of struts within the virtual volume such that each of the first plurality of struts has an average cross-sectional diameter that is smaller than an average cross-sectional diameter of each of the second plurality of struts. The method further includes thickening each of the first plurality of struts and the second plurality of struts within the virtual volume such that each of the first plurality of voids has an average internal diameter that is smaller than an average internal diameter of each of the second plurality of voids. The method still further includes thickening each of the first plurality of struts and the second plurality of struts within the virtual volume such that the first plurality of struts and the first plurality of voids have an overall material density that is approximately equal to the second plurality of struts and the second plurality of voids. Optionally, the solid surface is disposed at an external periphery of the virtual volume. Alternatively, the solid surface is disposed at an internal portion of the virtual volume. The method includes additively manufacturing the surgical implant device using the virtual volume including the designated solid surface and the located first plurality of struts that define the first plurality of voids and second plurality of struts that define the second plurality of voids. The method also includes defining a needle-populated porous surface adjacent to the solid surface. The method further includes additively manufacturing the solid surface and the needle-populated porous surface. The method includes additively manufacturing the solid surface and the needle-populated porous surface from one of a metallic material and a polymeric material.

BRIEF DESCRIPTION OF THE DRAWINGS

The present disclosure is illustrated and described with reference to the various drawings, in which like reference numbers are used to denote like device components/method steps, as appropriate, and in which:

FIG. 10 is a block diagram of a server which may be used in the cloud-based system of FIG. 9 or the like; and FIG. 11 is a block diagram of a user device which may be used in the cloud-based system of FIG. 9 or the like.

DESCRIPTION OF ILLUSTRATIVE EMBODIMENTS

Again, the present disclosure provides a surgical implant device, such as a spinal or other orthopedic implant device, that that incorporates both solid surfaces and an internal lattice volume. Specifically, an ALIF cage is provided as an example. This internal lattice volume utilizes more numerous, smaller pores and fine struts adjacent to the solid surfaces and less numerous, larger pores and thicker struts remote from the solid surfaces, thereby providing superior elasticity, bony ingrowth and purchase, and structural integrity and strength properties. Conventional internal voids and the like may also be provided for bone graft placement, etc. The surgical implant device of the present disclosure is developed using a CAD model and manufactured from a metallic (e.g., titanium) or polymeric (e.g., PEEK) material using an additive manufacturing process, such as 3D printing, or a more traditional manufacturing process.

Figure 1:
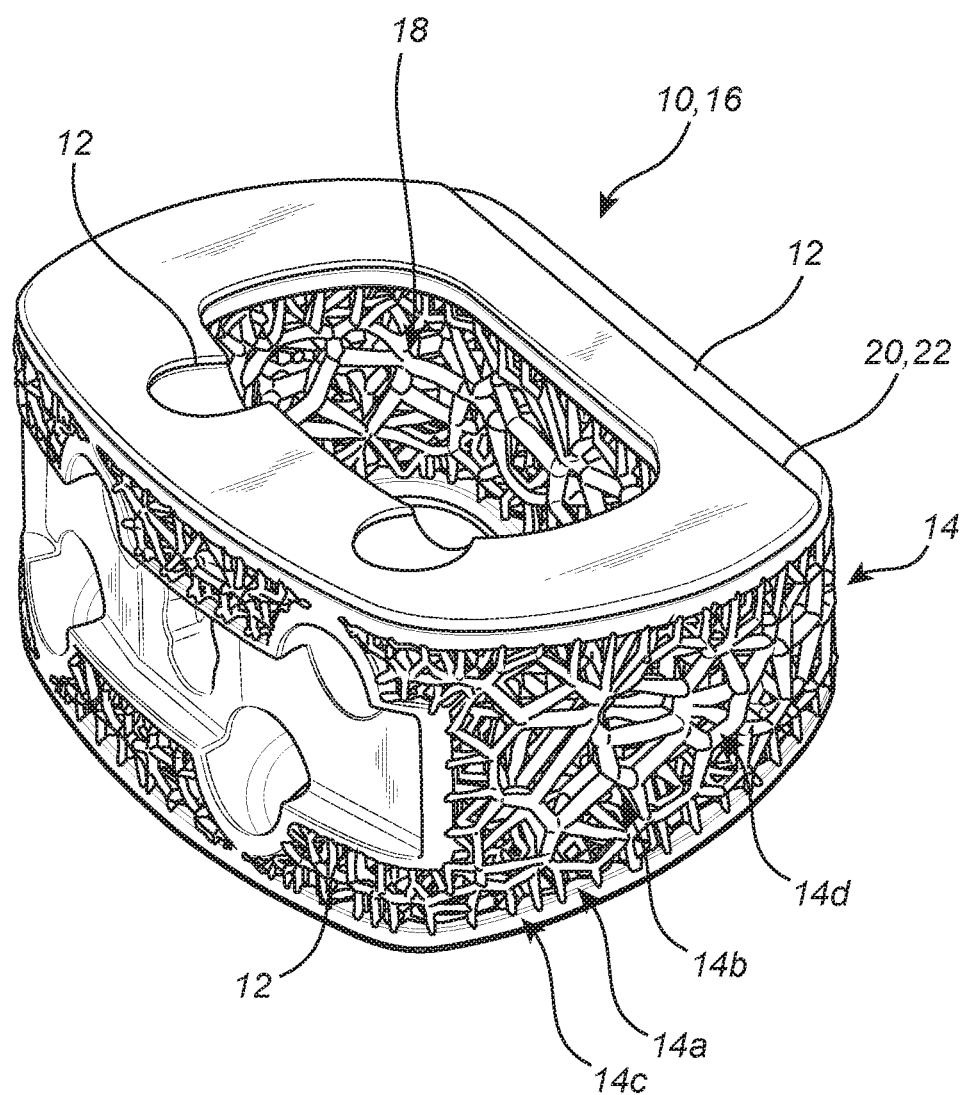
FIG. 1 is a perspective view of one illustrative embodiment of the implant device of the present disclosure.

Referring now specifically to FIG. 1, in one illustrative embodiment, the implant device 10 of the present disclosure includes one or more solid surfaces 12. These solid surfaces 12 represent bone contacting surfaces, screw hole surfaces, port surfaces, component receiving surfaces, and/or the like. The solid surfaces 12 may be arranged around the external periphery of the implant device 10, but may also be mid-device surfaces, and/or be arranged around the internal periphery of the implant device 10. As used herein, "solid" means having a relatively higher density and/or lower porosity than the adjacent lattice volume 14. Thus, the solid surfaces 12 may be integral metallic or polymeric surfaces, and/or may themselves include a lesser degree of porosity than the adjacent lattice volume 14. Solid surfaces 12 can surround the entire exterior, or only portions of the exterior, of the implant device 12. In the illustrative embodiment illustrated, an ALIF cage 16 is provided with solid surfaces 12 utilized for the bone contacting surfaces, the screw hole surfaces, and the screw retainer receiving surfaces. The lattice volume 14 is exposed around the external periphery of the ALIF cage 16, as well as around the internal periphery of the bone graft receiving void 18 formed at the center of the ALIF cage 16.

The interior of the implant device 10 consists of the lattice volume 14 disposed adjacent to/between the solid surfaces 12. The lattice volume 14 defines more numerous, smaller pores 14a adjacent to the solid surfaces 12 and less numerous, larger pores 14b remote from the solid surfaces 12. Correspondingly, the lattice volume 14 utilizes more numerous, finer struts 14c adjacent to the solid surfaces 12 and less numerous, thicker struts 14d remote from the solid surfaces 12. These pores 14a, 14b may have regular or random shapes, dimensions, and/or volumes. Likewise, these struts 14c, 14d may have regular or random cross-sectional shapes, lengths, and/or diameters.

Again, the implant device 10 of the present disclosure is developed using a CAD model and manufactured from a metallic (e.g., titanium) or polymeric (e.g., PEEK) material using an additive manufacturing process, such as 3D printing, or a more traditional manufacturing process. In the additive manufacturing case, the solid surfaces 12 and the lattice volume 14, including the struts 14c, 14d are integrally formed.

As is described in greater detail herein below, one or more of the solid surfaces 12 may include a porous surface 20 disposed thereon, opposite the lattice volume 14. This porous surface 20 may consist of a simple roughened or patterned surface that promotes bony purchase, or it may consist of a needle-populated secondary lattice volume 22 that further promotes bony purchase. Again, in the additive manufacturing case, the one or more of the solid surfaces 12 and the porous surface(s) 20, including the needle-populated secondary lattice volume(s) 22, are integrally formed. Thus, the implant device 10 includes the solid surfaces 12, the intervening lattice volume 14, and the bone contacting porous surface(s) 20.

Figure 2:
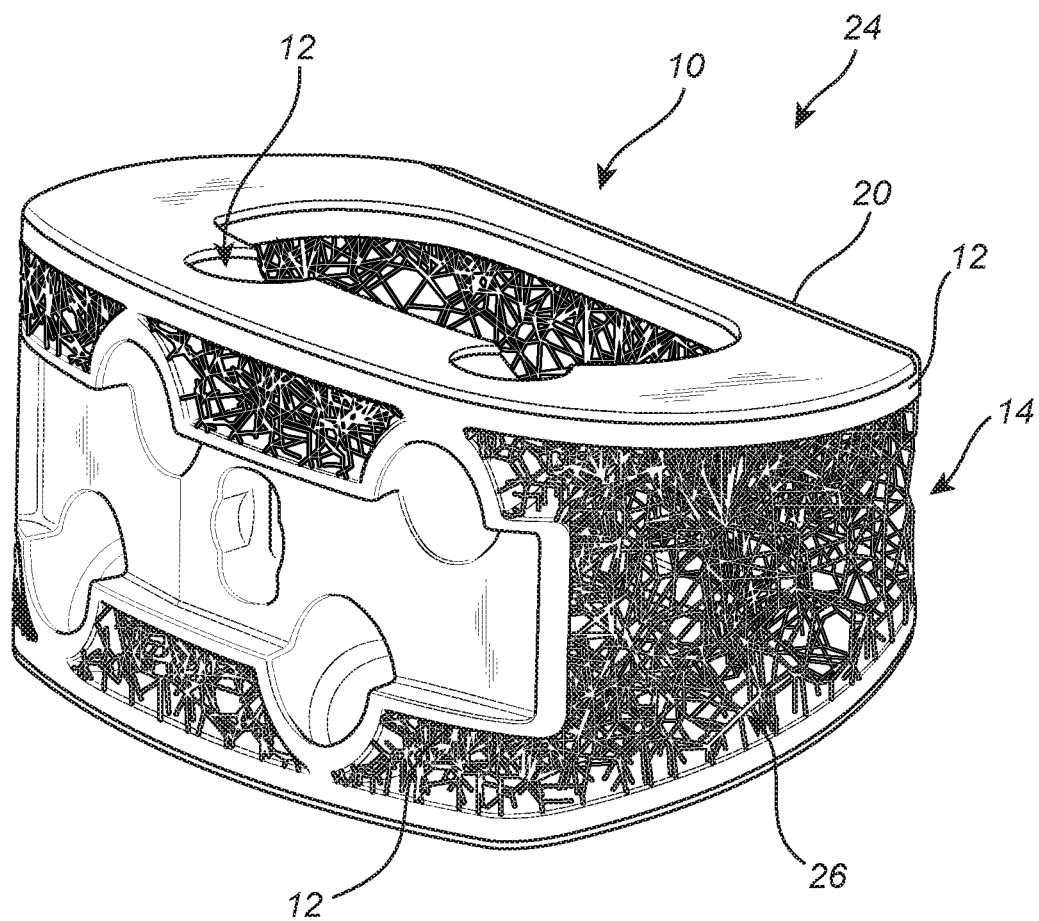
FIG. 2 is schematic diagram illustrating the overall methodology of generating the implant device of FIG. 1.

FIG. 2 is schematic diagram illustrating the overall methodology of generating the implant device 10 of FIG. 1. A CAD model 24 is provided that highlights three distinct regions: (1) the solid surfaces 12, (2) the lattice volume 14, and (3) the porous surface(s) 20. Using a software application, a Voronoi Volume Lattice (VVL) 26 is generated in the lattice volume 14, which replaces the solid material that would otherwise be present within the lattice volume 14. Generation of this VVL 26 requires the selection of random and/or ordered points within the lattice volume 14, which become the centers of the voids or pores of the VVL 26. Here, the ordered points may be manually generated, generated based on a solid geometry, and/or generated by a mathematical equation. To achieve the desired void or pore density variation, the lattice volume 14 may be segmented into sub-volumes or regions with VVL granularity that is more fine in a sub-volume adjacent to a solid surface 12 and more coarse in a sub-volume remote from a solid surface 12, for example, provided the VVL 26 is interconnected at the sub-volume interfaces. Preferably, two discrete sets of points are selected and utilized to generate the VVL 26.

Figure 3:
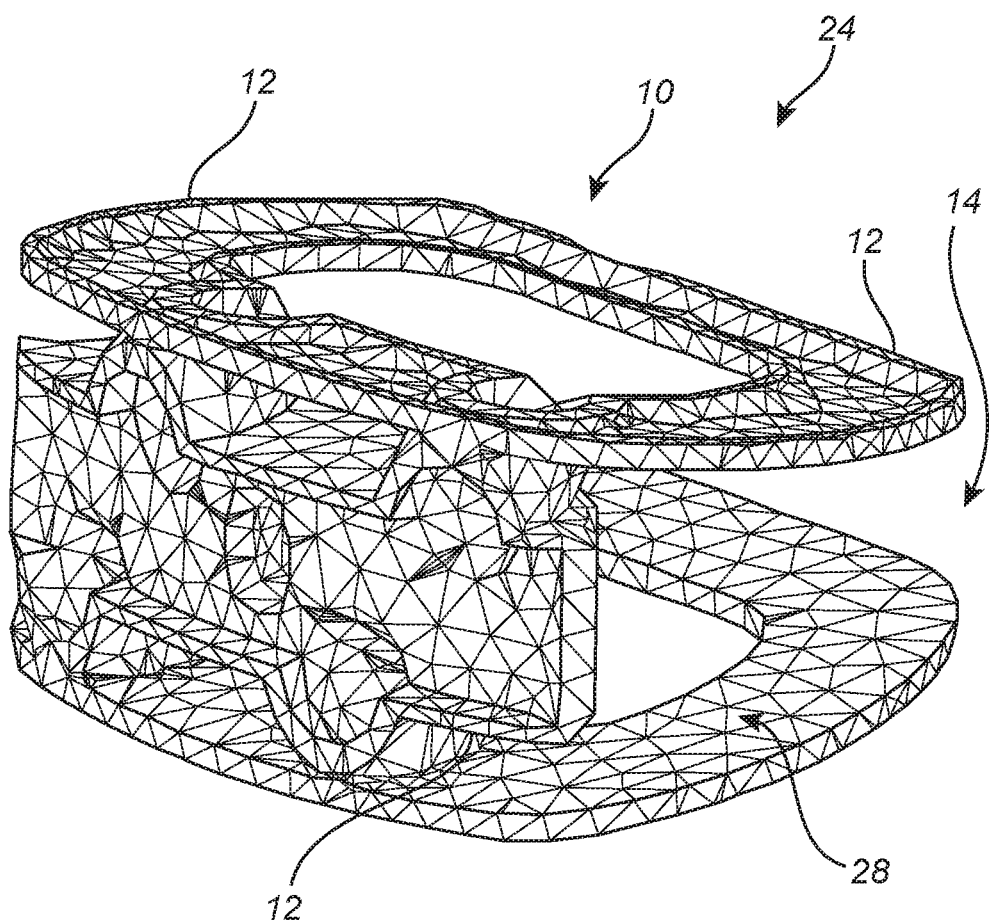
FIG. 3 is schematic diagram illustrating a mesh generation step in the overall methodology of FIG. 2.

Referring now specifically to FIG. 3, the first discrete set of points 32 (FIG. 4) is selected by applying a relatively fine virtual mesh 28 to the lattice volume 14. This virtual mesh 28 may be uniform and utilizes edge lengths on the order of 1.75-2 mm, for example, with the virtual mesh intersecting the solid surfaces 12. It will be readily apparent to those of ordinary skill in the art that other dimensions may be used equally.

Figure 4:
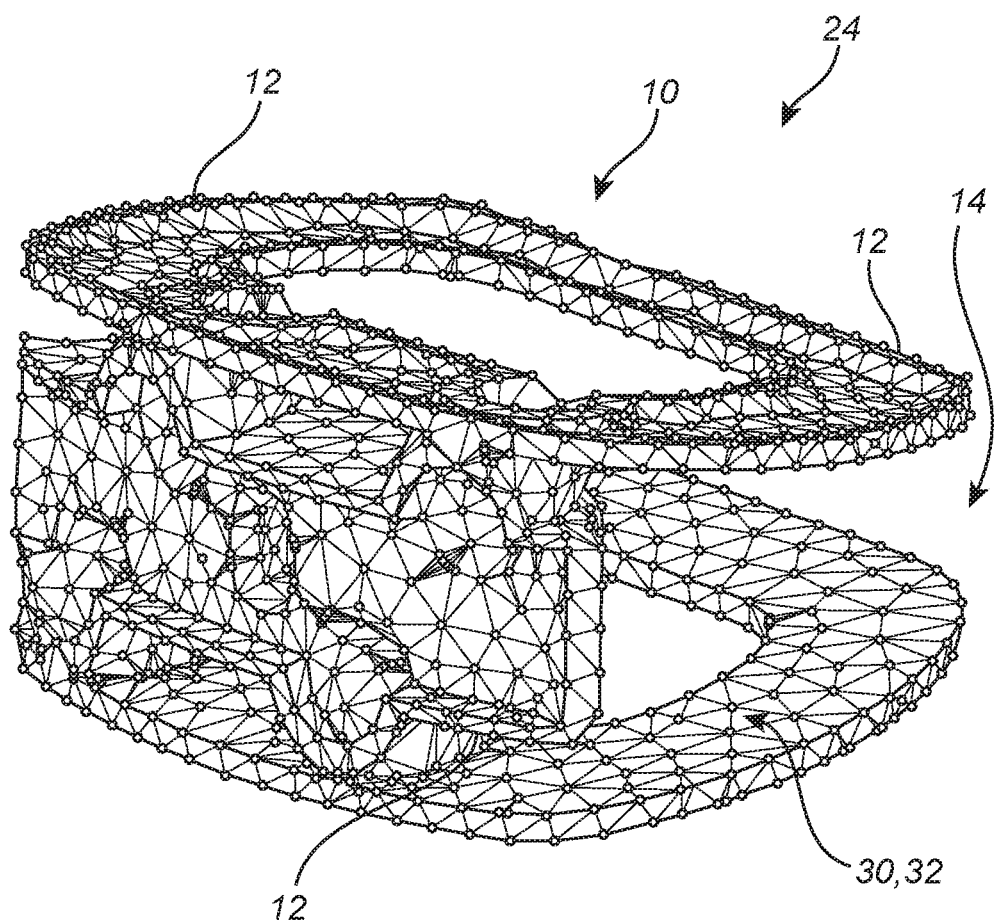
FIG. 4 is schematic diagram illustrating a first point selection step in the overall methodology of FIG. 2.

Referring now specifically to FIG. 4, the vertices 30 of the virtual mesh 28 (FIG. 3) with the solid surface 12 are then selected as the first discrete set of points 32.

Figure 5:
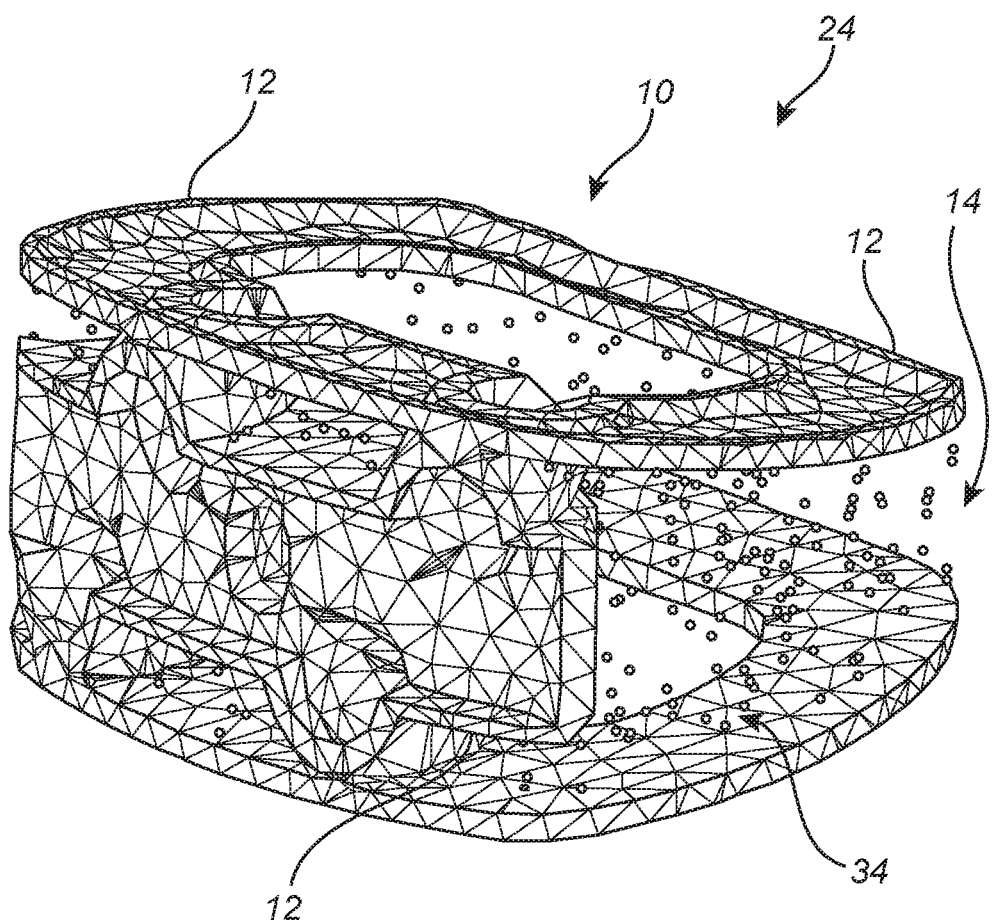
FIG. 5 is schematic diagram illustrating a second point selection step in the overall methodology of FIG. 2.

Referring now specifically to FIG. 5, the second discrete set of points 34 is selected or generated at random within the lattice volume 14, and are spaced by about 3 mm adjacent to the solid surfaces 12 and by about 4 mm remote from the solid surfaces 12. It will be readily apparent to those of ordinary skill in the art that other dimensions may be used equally.

Figure 6:
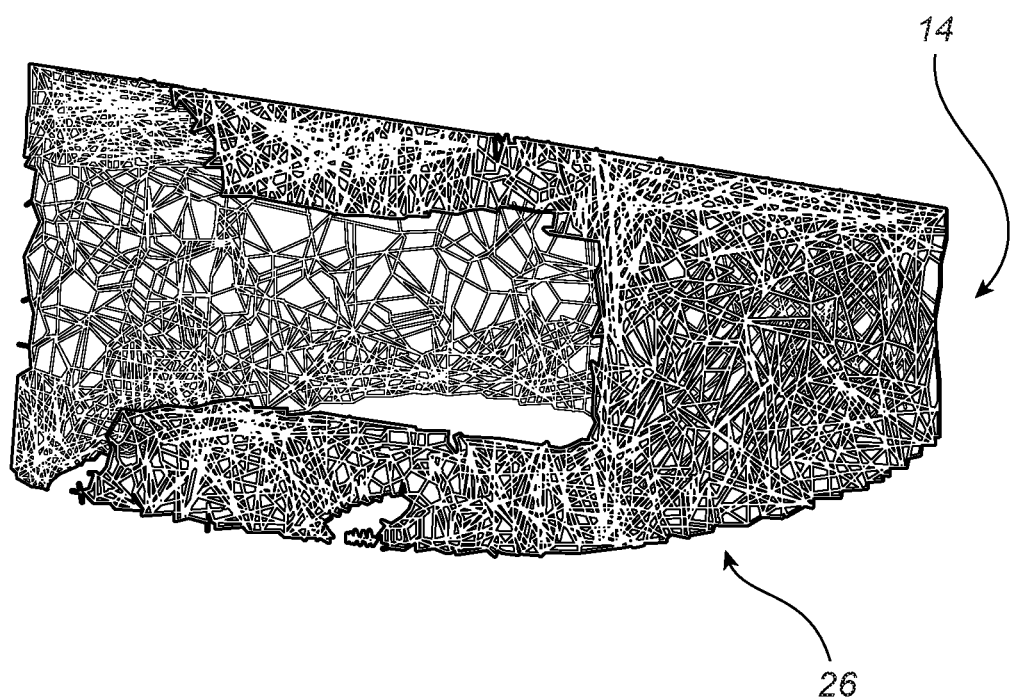
FIG. 6 is schematic diagram illustrating a lattice generation step in the overall methodology of FIG. 2.

Referring now specifically to FIG. 6, the first discrete set of points 32 (FIG. 4) and the second discrete set of points 34 (FIG. 5) are combined and used to generate the VVL 26, with the points 32, 34 representing the centers of the voids or pores (or, alternatively, the intersections of the struts of the VVL 26). The VVL 26 is then trimmed to fit the lattice volume 14. The result is a skeleton of the lattice volume 14. With all struts having the same cross-sectional diameter, the lattice volume 14 is thicker and less porous adjacent to the solid surfaces 12 (FIGS. 1-5) and finer and more porous remote from the solid surfaces 12. Because more points 32 and voids or pores are provided adjacent to the solid surfaces 12.

Figure 7:
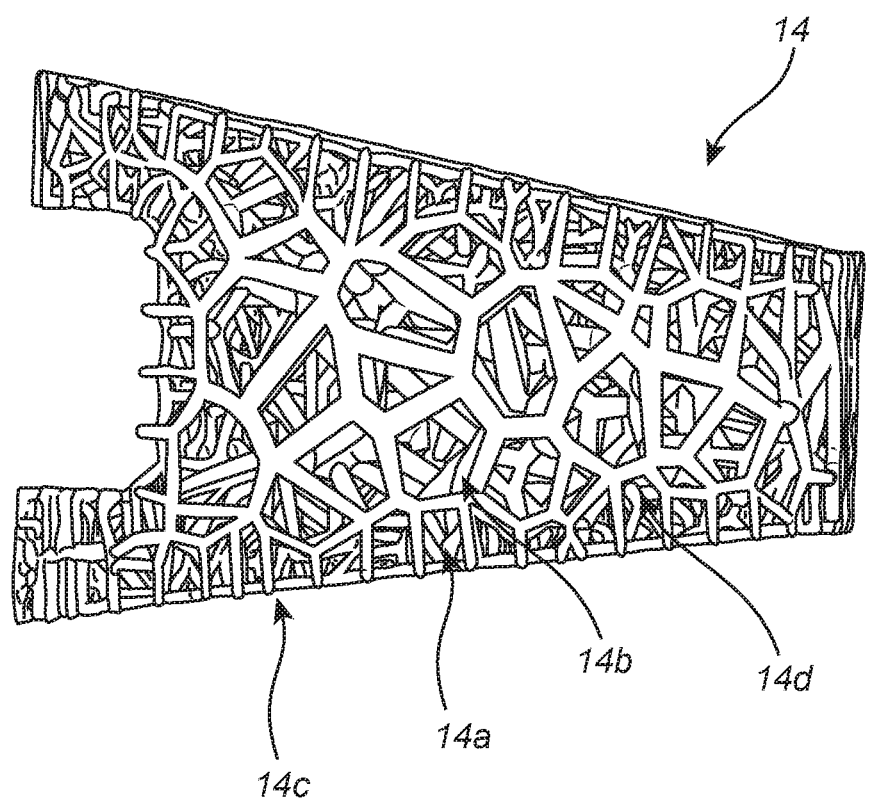
FIG. 7 is schematic diagram illustrating a strut thickening step in the overall methodology of FIG. 2.

Referring now specifically to FIG. 7, the skeleton of the lattice volume 14 is thickened. The struts 14c adjacent to the solid surfaces 12 (FIGS. 1-5) are increased to about 0.45 mm, for example, while the struts 14d remote from the solid surfaces 12 are increased to about 1 mm, for example. It will be readily apparent to those of ordinary skill in the art that other dimensions may be used equally. Further, the thickness of a given strut 14c, 14d may be varied along its length. Because the smaller struts 14c adjacent to the solid surfaces 12 surround smaller, more dense pores 14a, and the larger struts 14d remote from the solid surfaces 12 surround larger, less dense pores 14b, the two regions have comparable in percent porosity, which may be 60-85%, for example. It will be readily apparent to those of ordinary skill in the art that other porosities may be used equally. The struts 14c, 14d may have any suitable cross-sectional shape, such as circular, oval, triangular, square, rectangular, pentagonal, octagonal, irregular, etc.

Figure 8:
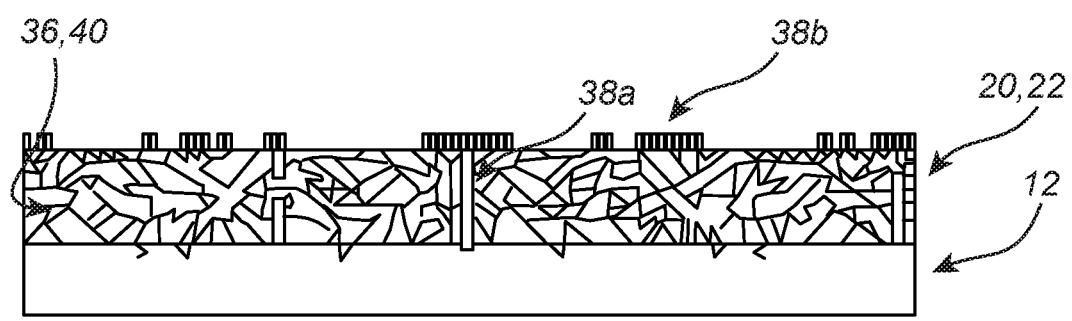
FIG. 8 is a schematic diagram illustrating one illustrative embodiment of the needle-populated porous structure that may cover the exterior of the implant device of FIG. 1.

FIG. 8 is a schematic diagram illustrating one illustrative embodiment of the needle-populated porous structure 22 that may cover the exterior of the implant device 10 (FIGS. 1-5). The implant device 10 may include at least one of the following: a primary structure 12; and at least one secondary lattice or porous surface portion 36 formed on at least one exterior portion of the primary structure 12, the at least one surface portion 36 located such that it engages with a patient's bone when the implant 10 is implanted in a patient. Such needle-populated, metallic surface portion 22 may contain, for example, a collection of at least fifty, a hundred, two hundred, five-hundred or more needles 38a, 38b, and may be further characterized by at least one, two, three, four, five or more of the following characteristics: (a) the needles 38a, 38b in the collection are all oriented substantially normal to the surface portion 36; (b) the needles 38a, 38b in the collection are all oriented in substantially the same direction, with the direction being other than normal to the surface portion 36; (c) the needles 38a, 38b in the collection are all oriented in substantially the same direction, with the direction being other than normal to the surface portion 36, but within 15 degrees from the normal direction; (d) the needles 38a, 38b in the collection are all oriented in substantially the same direction, with the direction being other than normal to the surface portion 36, and more than 15 degrees from the normal direction; (e) the collection includes needles 38a, 38b oriented in at least three different directions relative to the surface portion 36; (f) the collection includes needles 38a, 38b oriented in at least five different directions relative to the surface portion 36, with all of the needles oriented within 20 degrees from the surface portion normal direction; (g) all of the needles 38a, 38b in the collection have substantially the same height; (h) the collection includes needles 38a, 38b of at least three different heights; (i) all of the needles 38a, 38b in the collection have substantially the same shape; (j) the collection includes needles 38a, 38b of at least two different shapes; (k) the needles 38a, 38b are distributed substantially uniformly over the surface portion 36; (l) the needles 38a, 38b are distributed non-uniformly over the surface portion 36; (m) all of the needles 38a in the collection are anchored to the primary structure 12; (n) most of the needles 38a in the collection are anchored to the primary structure 12; (o) most of the needles 38b in the collection are anchored to structural elements contained within an osteo-porous, osteo-derived or trabecular coating 36 on the at least one exterior portion of the primary structure 12; and/or (p) all of the needles 38b in the collection are anchored to structural elements contained within an osteo-porous, osteo-derived or trabecular coating 36 on the at least one exterior portion of the primary structure 12. The at least one exterior portion 22 preferably includes at least one osteo-porous surface 36, which may comprise at least one osteo-derived surface 36. The at least one osteo-porous surface 36 and the needles 38a, 38b may be simultaneously formed by an additive manufacturing process.

The exemplary manufacturing flow starts with a spongy bone sample, which is micro-scanned to obtain 3D scan data, which is then processed into solid model data representing an osteo-porous or osteo-derived texture. This texture data is then combined with data representing the overall implant geometry to create a fabrication file for use by any of the manufacturing steps that follow. The fabrication file may utilize any recognizable solid model specification, such as ".amf" format or ".stl" format, and may be embodied on any sort of permanent, non-transitory storage medium (e.g., CD, CD-ROM, flash), semi-permanent (e.g., SRAM) or transitory (e.g., DRAM) storage medium, or embodied in a coded data signal.

An additional step is taken that adds outwardly-protruding "needles" 38a, 38b on the outer surface(s) of the osteo-porous and/or osteo-derived coating(s) 36. Such needles 38a, 38b substantially increase the coefficient of friction of the implant surface 22. Having a high coefficient of friction is clinically advantageous because it provides stronger initial fixation, which is important before bone is able to grow onto/into the porous structure 20. Such needles 38a, 38b can be uniformly or non-uniformly distributed along the porous surface. Likewise, various shapes for the needles 38a, 38b are possible, including rectangular, pyramidal, conical, tube-shaped, barbed, etc. Also, the needles 38a, 38b need not be oriented exactly normal to the exterior surface, but are preferably oriented in a substantially normal (e.g., within +/−15 degrees from normal) orientation. Furthermore, the orientation and/or shape of all needles 38a, 38b need not be the same, and the needles 38a, 38b may be rendered on selected portions, or the entirety, of the exterior coated surface(s) 20.

The methodology generates and provides a surface 22 that includes the implant body 12 and a porous layer 36 that is disposed directly adjacent to the implant body 12. The porous layer 36 can be additively manufactured on top of the implant body 12, or can be additively manufactured with the implant body 12. The porous layer 36 consists of a bone-interfacing lattice 40 of macroscopic, randomly distributed stochastic struts of various thicknesses, shapes, and intersection points. This lattice 40 is comparable to cancellous bone in terms of pore size and overall porosity, thus it elicits a favorable bone response when applied to the bone-opposition surfaces of the associated implant 10 to which it is applied. The needles 38a, 38b are additively manufactured with the porous layer 36 and/or the implant body 12 and some or all of the needles 38a protrude from and are anchored directly to the implant body 12, through the porous layer 36, and from the bone-opposition surface of the porous layer 36, forming regularly or randomly-arranged friction structures protruding from the bone-opposition surface of the porous layer 36. This provides advantageous needle strength and stability. Within the porous layer 36, these penetrating needles 38a are integrally formed with or otherwise anchored to adjacent of the struts of the lattice 40, again providing advantageous needle strength and stability. In one preferred embodiment, all needles 38a are planted 0.004-0.006 in. into the solid substrate, either physically or for behavioral modeling purposes (having a corresponding support stiffness), and extend about 0.008 in. above the bone-opposition surface of the porous layer 36, with a plurality of intervening lattice strut connections along the length of each needle 38a. Here, the needles 38a are 0.2 mm×0.2 mm rectangular prisms with constant cross-sections, for example. The preferred needle density is 0.3 needles/mm$^2$ or 1 needle 38a every 3.33 mm$^2$ for optimal bone friction engagement. The needles 38a are largely disposed normal to the bone-opposition surface of the porous layer 36 and the implant body 12, but may be angled with respect to one another due to curvature of the bone-opposition surface of the porous layer 36 and the implant body 12. The finished porous layer-needle construct is blasted with calcium phosphate or otherwise surface treated to promote roughness of the resulting bone-engagement structure. Alternatively, an osteo-porous, osteo-derived, and/or trabecular coating 36 with needles 38b anchored only to the bone-opposition surface of the osteo-porous, osteo-derived, and/or trabecular coating 36 and not the underlying implant body 12 may be utilized.

Slightly irregular secondary lattices 40 are ideally adapted for additive manufacturing in accordance with the present disclosure. Node perturbation refers to the location of intersecting struts. Such intersection locations can be randomized such that the node deviates from a uniform lattice by a randomized distance or degree. Strut size randomization refers to a deviation in cross-sectional dimension (e.g., strut diameter), as well as shape and length. Discrete struts in a lattice could have different cross-sectional sizes, or the struts could have a diameter gradient from one end to the other. These parameters can be randomized for greater diversity in the lattice's geometry. Such slightly-irregular lattices can be used to fabricate any sort of medical implant for which regular lattices might otherwise be used.

It should be understood that the novel structures disclosed and enabled by the present disclosure are not limited exclusively to those manufactured using additive manufacturing. Indeed, as persons skilled in the art will appreciate, other known surface modification techniques may be used to produce the osteoporous, osteo-derived, and/or needle-containing textures of the inventive implants.

The methodology of the present disclosure provides a surface that includes the implant body (or "melt") and a porous layer (or "structure") that is disposed directly adjacent to the implant body. The porous layer can be additively manufactured on top of the implant body, or can be additively manufactured with the implant body. The porous layer consists of a bone-interfacing lattice of macroscopic, randomly distributed stochastic struts of various thicknesses, shapes, and intersection points. This lattice is comparable to cancellous bone in terms of pore size and overall porosity, thus it elicits a favorable bone response when applied to the bone-opposition surfaces of the associated implant to which it is applied. The generation of the overall structure is accomplished through several CAD modeling programs in the following data preparation process flow. CAD modeling software is used to generate the design envelope (i.e. the volumes) and spatial relationship (i.e. the overlap) of the various structural elements. The overall structure is comprised of three specific volume elements: the melt volume, the structure volume, and the needle volume. The melt volume is the CAD volume that defines the solid substrate that the structure and needles interface and overlap to ensure a mechanical interface during the additive manufacturing process. For most scenarios, the melt volume is the bulk of the device. The structure volume is the CAD volume that defines the virtual boundary conditions for which the random, stochastic structure will be generated. The structure volume is purely solid and without any lattice. The needle volume is the CAD volume that defines the virtual boundary conditions for which the random, protrusions will extend beyond the regions of the structure volume. The needle volume is purely solid and without any needles (i.e. protrusions). A CAD assembly combines the melt volume, structure volume, and needle volume part models. The structure volume and needle volume elements overlap with the melt volume within the defined coordinate system through the mate interface GUI. This overlap is based on the resolution and accuracy of the intended additive manufacturing technology for which the device will be manufactured. After the CAD assembly has been defined, the models are exported as a ".stl" file format. The files are imported into additional CAD software and used to generate the structure and needles from the structure volume and needle volume elements that were previously defined. Using the structure volume, the user executes the graphical user interface (GUI) algorithm. This algorithm applies a unit cell within a defined volume relative to the CAD environment's coordinate system. The algorithm executes a Boolean operation between the array of unit cells and the structure-volume to yield only the portions of the unit cell within the volume. The overall structure utilizes a porous structure unit cell of defined dimensions, shape, and volume. The algorithm is used to duplicate the porous structure unit cell as an array across the structure volume element and then trim the unit cells within the boundaries of the structure volume. The result is the structure; a random, stochastic lattice that fills the volume of the original structure volume envelope. Similar to structure generation, needles are generated via an intersection Boolean operation between the needle volume element and a pre-programmed file that is generated by an equation-driven algorithm. The pre-programmed needle-element is imported into the CAD software and spatially-aligned with the needle volume. The Boolean is executed and the resulting geometry is an array of randomly located needles (i.e. protrusions) within the boundaries previously defined by the needle volume. After successfully generating the structure and needles, the components are exported as ".stl" files. The files are then imported into additive manufacturing technology-specific software programs in preparation for the additive manufacturing process. The technology-specific software programs slice the CAD models at a defined thickness acceptable for the additive manufacturing equipment, define the sequence of part build order, and apply exposure strategies. The result of these programs is a build file that is imported and executed on the additive manufacturing machine to yield a physical part.

It is to be recognized that, depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Figure 9:
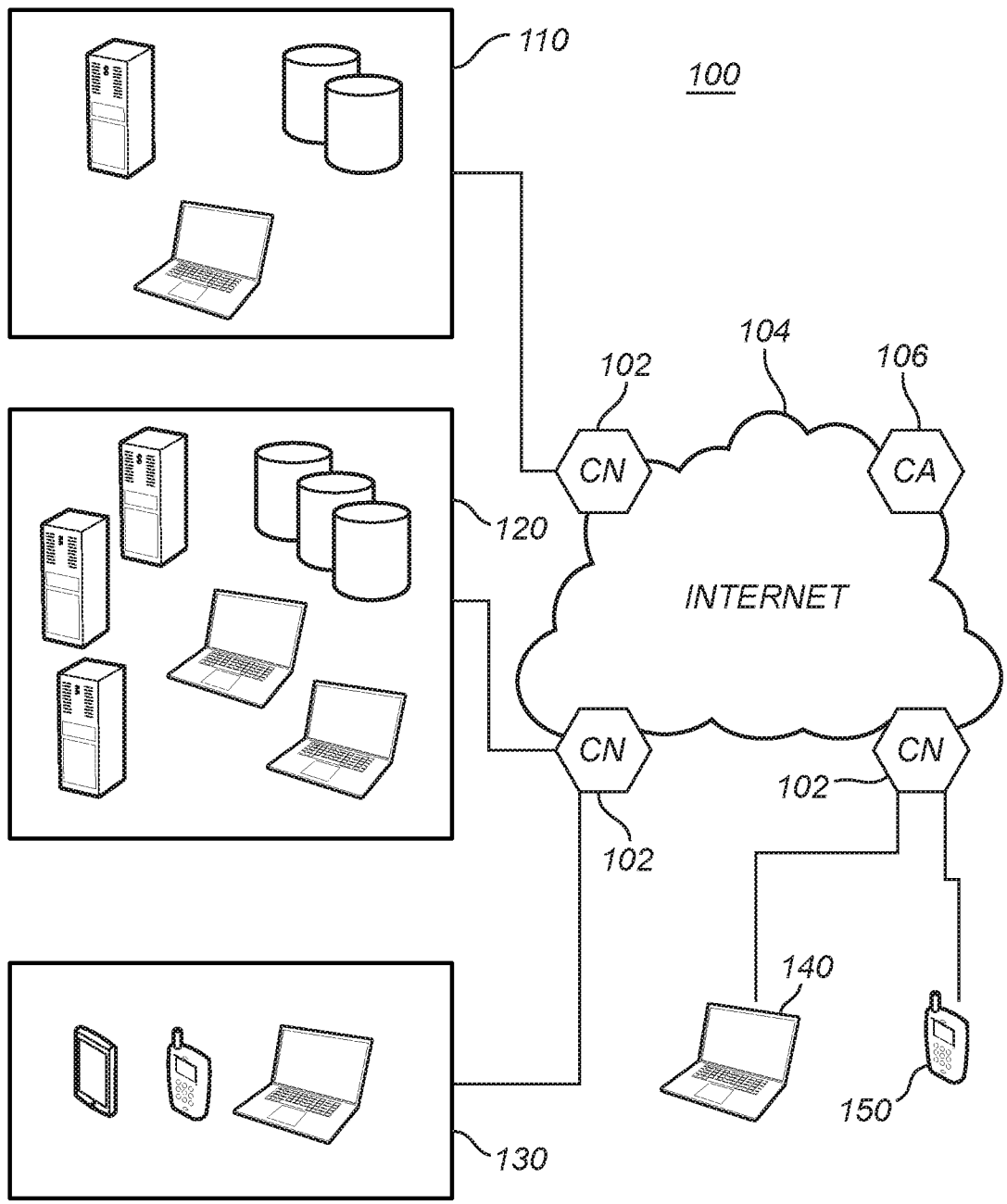
FIG. 9 is a network diagram of a cloud-based system for implementing various cloud-based operations of the present disclosure.
Figure 10:
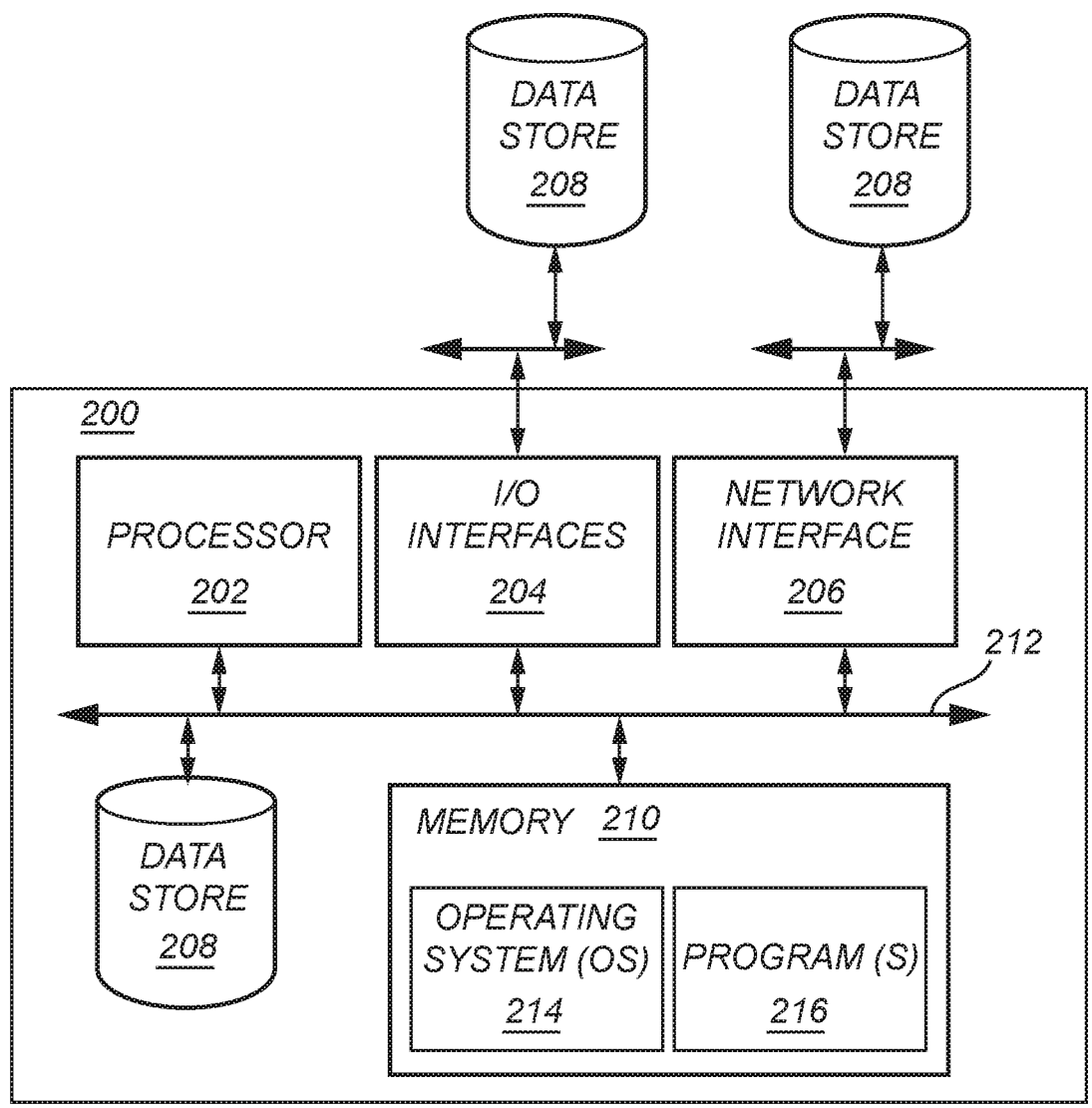

FIG. 9 is a network diagram of a cloud-based system 100 for implementing various cloud-based services of the present disclosure. The cloud-based system 100 includes one or more cloud nodes (CNs) 102 communicatively coupled to the Internet 104 or the like. The cloud nodes 102 may be implemented as a server 200 (as illustrated in FIG. 10) or the like and can be geographically diverse from one another, such as located at various data centers around the country or globe. Further, the cloud-based system 100 can include one or more central authority (CA) nodes 106, which similarly can be implemented as the server 200 and be connected to the CNs 102. For illustration purposes, the cloud-based system 100 can connect to a regional office 110, headquarters 120, various employee's homes 130, laptops/desktops 140, and mobile devices 150, each of which can be communicatively coupled to one of the CNs 102. These locations 110, 120, and 130, and devices 140 and 150 are shown for illustrative purposes, and those skilled in the art will recognize there are various access scenarios to the cloud-based system 100, all of which are contemplated herein. The devices 140 and 150 can be so-called road warriors, i.e., users off-site, on-the-road, etc. The cloud-based system 100 can be a private cloud, a public cloud, a combination of a private cloud and a public cloud (hybrid cloud), or the like.

Again, the cloud-based system 100 can provide any functionality through services such as software-as-a-service (SaaS), platform-as-a-service, infrastructure-as-a-service, security-as-a-service, Virtual Network Functions (VNFs) in a Network Functions Virtualization (NFV) Infrastructure (NFVI), etc. to the locations 110, 120, and 130 and devices 140 and 150. Previously, the Information Technology (IT) deployment model included enterprise resources and applications stored within an enterprise network (i.e., physical devices), behind a firewall, accessible by employees on site or remote via Virtual Private Networks (VPNs), etc. The cloud-based system 100 is replacing the conventional deployment model. The cloud-based system 100 can be used to implement these services in the cloud without requiring the physical devices and management thereof by enterprise IT administrators.

Cloud computing systems and methods abstract away physical servers, storage, networking, etc., and instead offer these as on-demand and elastic resources. The National Institute of Standards and Technology (NIST) provides a concise and specific definition which states cloud computing is a model for enabling convenient, on-demand network access to a shared pool of configurable computing resources (e.g., networks, servers, storage, applications, and services) that can be rapidly provisioned and released with minimal management effort or service provider interaction. Cloud computing differs from the classic client-server model by providing applications from a server that are executed and managed by a client's web browser or the like, with no installed client version of an application necessarily required. Centralization gives cloud service providers complete control over the versions of the browser-based and other applications provided to clients, which removes the need for version upgrades or license management on individual client computing devices. The phrase "software as a service" (SaaS) is sometimes used to describe application programs offered through cloud computing. A common shorthand for a provided cloud computing service (or even an aggregation of all existing cloud services) is "the cloud." The cloud-based system 100 is illustrated herein as one example embodiment of a cloud-based system, and those of ordinary skill in the art will recognize the systems and methods described herein are not necessarily limited thereby.

FIG. 10 is a block diagram of a server 200, which may be used in the cloud-based system 100 (FIG. 9), in other systems, or standalone. For example, the CNs 102 (FIG. 9) and the central authority nodes 106 (FIG. 9) may be formed as one or more of the servers 200. The server 200 may be a digital computer that, in terms of hardware architecture, generally includes a processor 202, input/output (I/O) interfaces 204, a network interface 206, a data store 208, and memory 210. It should be appreciated by those of ordinary skill in the art that FIG. 10 depicts the server 200 in an oversimplified manner, and a practical embodiment may include additional components and suitably configured processing logic to support known or conventional operating features that are not described in detail herein. The components (202, 204, 206, 208, and 210) are communicatively coupled via a local interface 212. The local interface 212 may be, for example, but is not limited to, one or more buses or other wired or wireless connections, as is known in the art. The local interface 212 may have additional elements, which are omitted for simplicity, such as controllers, buffers (caches), drivers, repeaters, and receivers, among many others, to enable communications. Further, the local interface 212 may include address, control, and/or data connections to enable appropriate communications among the aforementioned components.

The processor 202 is a hardware device for executing software instructions. The processor 202 may be any custom made or commercially available processor, a central processing unit (CPU), an auxiliary processor among several processors associated with the server 200, a semiconductor-based microprocessor (in the form of a microchip or chipset), or generally any device for executing software instructions. When the server 200 is in operation, the processor 202 is configured to execute software stored within the memory 210, to communicate data to and from the memory 210, and to generally control operations of the server 200 pursuant to the software instructions. The I/O interfaces 204 may be used to receive user input from and/or for providing system output to one or more devices or components.

The network interface 206 may be used to enable the server 200 to communicate on a network, such as the Internet 104 (FIG. 9). The network interface 206 may include, for example, an Ethernet card or adapter (e.g., 10BaseT, Fast Ethernet, Gigabit Ethernet, or 10 GbE) or a Wireless Local Area Network (WLAN) card or adapter (e.g., 802.11a/b/g/n/ac). The network interface 206 may include address, control, and/or data connections to enable appropriate communications on the network. A data store 208 may be used to store data. The data store 208 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 208 may incorporate electronic, magnetic, optical, and/or other types of storage media. In one example, the data store 208 may be located internal to the server 200, such as, for example, an internal hard drive connected to the local interface 212 in the server 200. Additionally, in another embodiment, the data store 208 may be located external to the server 200 such as, for example, an external hard drive connected to the I/O interfaces 204 (e.g., a SCSI or USB connection). In a further embodiment, the data store 208 may be connected to the server 200 through a network, such as, for example, a network-attached file server.

The memory 210 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 210 may incorporate electronic, magnetic, optical, and/or other types of storage media. Note that the memory 210 may have a distributed architecture, where various components are situated remotely from one another but can be accessed by the processor 202. The software in memory 210 may include one or more software programs, each of which includes an ordered listing of executable instructions for implementing logical functions. The software in the memory 210 includes a suitable operating system (O/S) 514 and one or more programs 216. The operating system 214 essentially controls the execution of other computer programs, such as the one or more programs 216, and provides scheduling, input-output control, file and data management, memory management, and communication control and related services. The one or more programs 216 may be configured to implement the various processes, algorithms, methods, techniques, etc. described herein.

It will be appreciated that some embodiments described herein may include one or more generic or specialized processors ("one or more processors") such as microprocessors; central processing units (CPUs); digital signal processors (DSPs); customized processors such as network processors (NPs) or network processing units (NPUs), graphics processing units (GPUs), or the like; field programmable gate arrays (FPGAs); and the like along with unique stored program instructions (including both software and firmware) for control thereof to implement, in conjunction with certain non-processor circuits, some, most, or all of the functions of the methods and/or systems described herein. Alternatively, some or all functions may be implemented by a state machine that has no stored program instructions, or in one or more application-specific integrated circuits (ASICs), in which each function or some combinations of certain of the functions are implemented as custom logic or circuitry. Of course, a combination of the aforementioned approaches may be used. For some of the embodiments described herein, a corresponding device in hardware and optionally with software, firmware, and a combination thereof can be referred to as "circuitry configured or adapted to," "logic configured or adapted to," etc. perform a set of operations, steps, methods, processes, algorithms, functions, techniques, etc. on digital and/or analog signals as described herein for the various embodiments.

Moreover, some embodiments may include a non-transitory computer-readable storage medium having computer-readable code stored thereon for programming a computer, server, appliance, device, processor, circuit, etc. each of which may include a processor to perform functions as described and claimed herein. Examples of such computer-readable storage mediums include, but are not limited to, a hard disk, an optical storage device, a magnetic storage device, a Read-Only Memory (ROM), a Programmable Read-Only Memory (PROM), an Erasable Programmable Read-Only Memory (EPROM), an Electrically Erasable Programmable Read-Only Memory (EEPROM), flash memory, and the like. When stored in the non-transitory computer-readable medium, software can include instructions executable by a processor or device (e.g., any type of programmable circuitry or logic) that, in response to such execution, cause a processor or the device to perform a set of operations, steps, methods, processes, algorithms, functions, techniques, etc. as described herein for the various embodiments.

Figure 11:
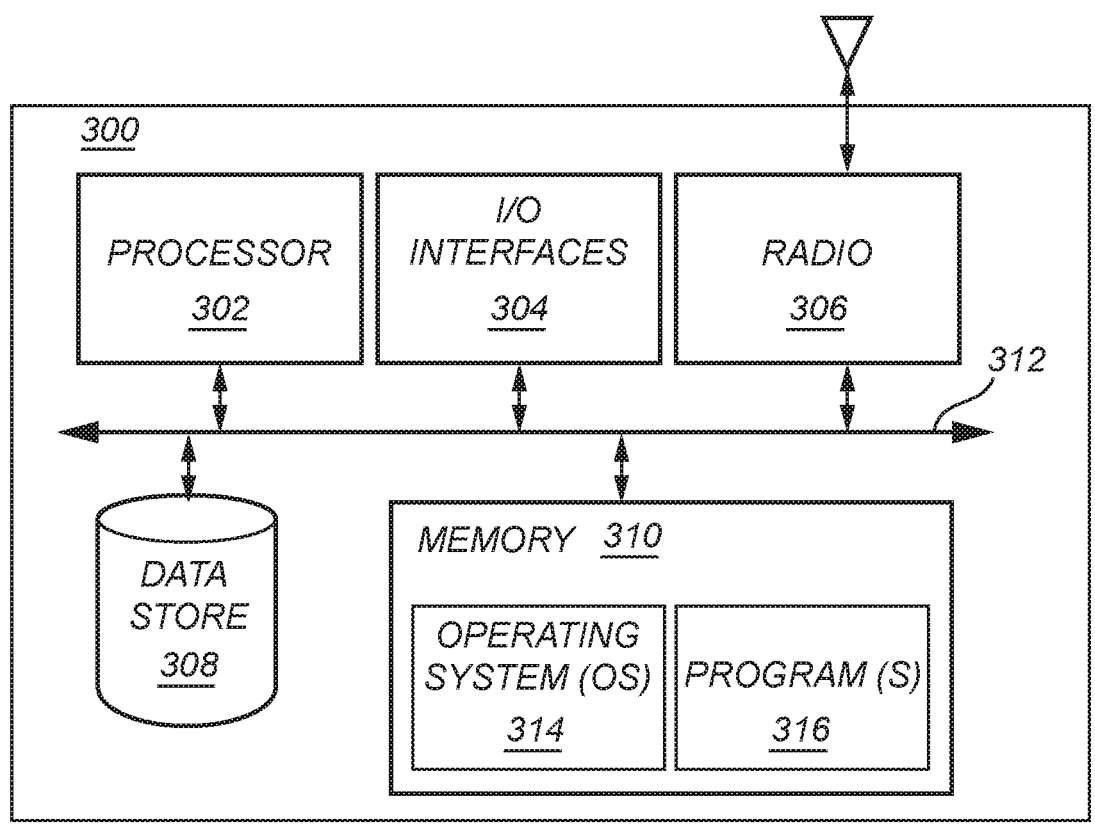

FIG. 11 is a block diagram of a user device 300, which may be used in the cloud-based system 100 (FIG. 9) or the like. Again, the user device 300 can be a smartphone, a tablet, a smartwatch, an Internet of Things (IoT) device, a laptop, a virtual reality (VR) headset, etc. The user device 300 can be a digital device that, in terms of hardware architecture, generally includes a processor 302, I/O interfaces 304, a radio 306, a data store 308, and memory 310. It should be appreciated by those of ordinary skill in the art that FIG. 18 depicts the user device 300 in an oversimplified manner, and a practical embodiment may include additional components and suitably configured processing logic to support known or conventional operating features that are not described in detail herein. The components (302, 304, 306, 308, and 310) are communicatively coupled via a local interface 312. The local interface 312 can be, for example, but is not limited to, one or more buses or other wired or wireless connections, as is known in the art. The local interface 312 can have additional elements, which are omitted for simplicity, such as controllers, buffers (caches), drivers, repeaters, and receivers, among many others, to enable communications. Further, the local interface 312 may include address, control, and/or data connections to enable appropriate communications among the aforementioned components.

The processor 302 is a hardware device for executing software instructions. The processor 302 can be any custom made or commercially available processor, a CPU, an auxiliary processor among several processors associated with the user device 300, a semiconductor-based microprocessor (in the form of a microchip or chipset), or generally any device for executing software instructions. When the user device 300 is in operation, the processor 302 is configured to execute software stored within the memory 310, to communicate data to and from the memory 310, and to generally control operations of the user device 300 pursuant to the software instructions. In an embodiment, the processor 302 may include a mobile optimized processor such as optimized for power consumption and mobile applications. The I/O interfaces 304 can be used to receive user input from and/or for providing system output. User input can be provided via, for example, a keypad, a touch screen, a scroll ball, a scroll bar, buttons, a barcode scanner, and the like. System output can be provided via a display device such as a liquid crystal display (LCD), touch screen, and the like.

The radio 306 enables wireless communication to an external access device or network. Any number of suitable wireless data communication protocols, techniques, or methodologies can be supported by the radio 306, including any protocols for wireless communication. The data store 308 may be used to store data. The data store 308 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 308 may incorporate electronic, magnetic, optical, and/or other types of storage media.

Again, the memory 310 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 310 may incorporate electronic, magnetic, optical, and/or other types of storage media. Note that the memory 310 may have a distributed architecture, where various components are situated remotely from one another, but can be accessed by the processor 302. The software in memory 310 can include one or more software programs, each of which includes an ordered listing of executable instructions for implementing logical functions. In the example of FIG. 11, the software in the memory 310 includes a suitable operating system 314 and programs 316. The operating system 314 essentially controls the execution of other computer programs and provides scheduling, input-output control, file and data management, memory management, and communication control and related services. The programs 316 may include various applications, add-ons, etc. configured to provide end user functionality with the user device 300. For example, example programs 316 may include, but not limited to, a web browser, social networking applications, streaming media applications, games, mapping and location applications, electronic mail applications, financial applications, and the like. In a typical example, the end-user typically uses one or more of the programs 316 along with a network such as the cloud-based system 100 (FIG. 9).

Although the present disclosure is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following non-limiting claims for all purposes.

What is claimed is:

1. A surgical implant device, comprising:
an upper solid surface defining an upper bone contacting surface including an entire upper surface of the surgical implant device; and
a lower solid surface defining a lower bone contacting surface including an entire lower surface of the surgical implant device; and
a lattice structure disposed between the upper solid surface and the lower solid surface, wherein a first layer of the lattice structure fills a first full cross-section of the lattice structure and has a first thickness, the first layer comprising a first plurality of struts that define a first plurality of voids adjacent to one of the upper solid surface or the lower solid surface within an interior of the surgical implant device, a second layer of the lattice structure fills a second full cross-section of the lattice structure and has a second thickness, the second layer comprising a second plurality of struts that define a second plurality of voids adjacent to the other of the upper solid surface or the lower solid surface within the interior of the surgical implant device, and a third layer of the lattice structure fills a third full cross-section of the lattice structure and has a third thickness, the third layer comprising a third plurality of struts that define a third plurality of voids remote from each of the upper solid surface and the lower solid surface and within the interior of the surgical implant device, wherein each of the first plurality of struts and each of the second plurality of struts has an average cross-sectional diameter that is smaller than an average cross-sectional diameter of each of the third plurality of struts, wherein each of the first plurality of voids and each of the second plurality of voids has an average internal dimension that is smaller than an average internal dimension of each of the third plurality of voids,
wherein the first plurality of struts and the first plurality of voids are disposed between and coupled between one of the upper solid surface or the lower solid surface and/to the third plurality of struts and the third plurality of voids, and the second plurality of struts and the second plurality of voids are disposed between and coupled between the other of the upper solid surface or the lower solid surface and/to the third plurality of struts and the third plurality of voids such that the third layer of the lattice structure separates the first layer and the second layer of the lattice structure throughout the lattice structure, and
wherein each of the first plurality of struts and the first plurality of voids and the second plurality of struts and the second plurality of voids has an overall material density that is approximately equal to the third plurality of struts and the third plurality of voids.

2. The surgical implant device of claim 1, wherein the upper solid surface is disposed at and forms upper external periphery surfaces of the surgical implant device, and wherein the lower solid surface is disposed at and forms lower external periphery surfaces of the surgical implant device.

3. The surgical implant device of claim 1, wherein each of the upper solid surface, the lower solid surface, and the lattice structure are integrally formed.

4. The surgical implant device of claim 1, further comprising a porous surface disposed adjacent to at least one of the upper solid surface or the lower solid surface and opposite the lattice structure.

5. The surgical implant device of claim 4, wherein at least one of the upper solid surface or the lower solid surface and the porous surface are integrally formed.

6. The surgical implant device of claim 1, further comprising a screw receiving surface including a solid surface extending across a side edge of the surgical implant device between the upper solid surface and the lower solid surface.

7. The surgical implant device of claim 1, wherein the upper solid surface, the first layer of the lattice structure, the third layer of the lattice structure, the second layer of the lattice structure, and the lower solid surface are arranged and configured as consecutive layers of the surgical implant device.

8. The surgical implant device of claim 1, wherein each of the upper solid surface and the lower solid surface has a regional density that is greater than regional densities defined by any of the lattice structure, the first layer, the second layer, and the third layer.

9. The surgical implant device of claim 1, wherein each of the struts included in the first layer and the second layer of the lattice structure has the average cross-sectional diameter that is smaller than the average cross-sectional diameter of each of the struts included in the third layer of the lattice structure, and
wherein each of the first layer, the second layer, and the third layer has a regional porosity of 60-85%.

10. The surgical implant device of claim 1, wherein each of the voids defined within the first layer and the second layer of the lattice structure has the average internal dimension that is smaller than the average internal dimension of each of the voids defined within the third layer of the surgical implant device, and wherein each of the first layer, the second layer, and the third layer has a regional porosity of 60-85%.

* * * * *